United States Patent [19]

Weyl

[11] Patent Number: 5,755,941

[45] Date of Patent: May 26, 1998

[54] ELECTROCHEMICAL MEASURING ELEMENT

[75] Inventor: Helmut Weyl, Schwieberdingen, Germany

[73] Assignee: Robert Bosch GmbH, Stuttgart, Germany

[21] Appl. No.: 687,608

[22] PCT Filed: Dec. 18, 1995

[86] PCT No.: PCT/DE95/01809

§ 371 Date: Aug. 8, 1996

§ 102(e) Date: Aug. 8, 1996

[87] PCT Pub. No.: WO96/21148

PCT Pub. Date: Jul. 11, 1996

[30] Foreign Application Priority Data

Jan. 4, 1995 [DE] Germany ................ 195 00 147.8

[51] Int. Cl.[6] ................................................ G01N 27/407

[52] U.S. Cl. ........................ 204/424; 204/427; 204/428

[58] Field of Search ................................. 204/421–429

[56] References Cited

U.S. PATENT DOCUMENTS

| | | | |
|---|---|---|---|
| 3,891,529 | 6/1975 | Beesch | 204/428 |
| 4,121,989 | 10/1978 | Shum et al. | 204/428 |
| 4,128,469 | 12/1978 | Rohr et al. | 204/427 |
| 4,184,934 | 1/1980 | Bode et al. | 204/428 |
| 4,229,275 | 10/1980 | Habdas et al. | 204/426 |
| 4,253,302 | 3/1981 | Asno et al. | 204/428 |
| 4,569,748 | 2/1986 | Yamakawa et al. | 204/428 |
| 4,657,660 | 4/1987 | Sato et al. | 204/427 |
| 4,818,364 | 4/1989 | Weber et al. | 204/427 |
| 4,842,713 | 6/1989 | Stahl | 204/427 |
| 5,178,744 | 1/1993 | Nakazawa et al. | 204/427 |
| 5,228,975 | 7/1993 | Yamada et al. | 204/424 |

FOREIGN PATENT DOCUMENTS

| | | |
|---|---|---|
| 0520528 | 12/1992 | European Pat. Off. . |
| 2343428 | 3/1975 | Germany . |
| 2343429 | 3/1975 | Germany . |
| 3922331 | 1/1991 | Germany . |
| 4318789 | 12/1994 | Germany . |
| 4342731 | 2/1995 | Germany . |

OTHER PUBLICATIONS

Fujikura, JP 40 089562, Mar. 23, 1992, *Patent Abstracts of Japan*, vol. 16, No. 317, Jul. 10, 1992.

*Primary Examiner*—T. Tung
*Attorney, Agent, or Firm*—Spencer & Frank

[57] ABSTRACT

An electrochemical measuring element for determining oxygen content in exhaust gases of internal combustion engines includes a metallic housing; a sensor element which is a tube that is closed at one end, which is inserted into the metallic housing, and which forms a structural unit with the metallic housing; a seal composed of a glass sealing and a metallic sleeve, the glass sealing connecting the sensor element and the metallic sleeve in a gas-tight manner; and a ceramic sealing ring which is disposed between the sensor element and the metallic sleeve, wherein the glass sealing is inserted between the sensor element and the ceramic sealing ring, as well as between the ceramic sealing ring and the metallic sleeve, wherein the sensor element and the seal form a preassembled structural unit which can be inserted into the metallic housing, and wherein the metallic sleeve is welded to the metallic housing in a gas-tight manner.

9 Claims, 1 Drawing Sheet

1

ELECTROCHEMICAL MEASURING ELEMENT

BACKGROUND OF THE INVENTION

FIELD OF THE INVENTION

The invention is based on an electrochemical measuring element, particularly for determining the oxygen content in exhaust gases of internal combustion engines, having a sensor element in the form of a tube that is closed at one end and is inserted into a metallic housing having a seal. Electrochemical measuring elements are configured, for example, to include a sensor element with a so-called finger design. The sensor element is a solid electrolyte body configured as a closed tube and secured in a gas-tight manner inside a metallic housing. The finger sensors are divided into potential-free and potential-bound measuring elements. In potential-bound measuring elements, the conductor path of the outer electrode is contacted to the housing by means of an electrically-conductive sealing ring. In potential-free measuring sensors, each electrode connection is tapped separately, which does not permit electrical contacting with the housing. In both cases, a seal must be produced between the solid electrolyte body and the housing.

In potential-free measuring elements, the gas-tight and benzene-resistant mounting of the sensor element in the metallic housing is associated with special problems. To solve these problems, either a metallic sealing ring or an electrically-insulating, ceramic sealing ring is used. Ceramic sealing rings are not absolutely gas-tight and benzene-resistant. If metallic sealing rings are used, the conductor path extending on the outer surface of the solid electrolyte body, in the region of the sealing ring, must be covered with an electrically-insulating cover layer. A drawback, however, is the occurrence of pressure peaks that originate at the metallic sealing ring and damage the cover layer, thus reducing its insulating effect.

SUMMARY OF THE INVENTION

In contrast, the measuring element of the invention having the characterizing features of the main claim has the advantage that it permits the solid electrolyte body to be mounted in the metallic housing to be gas-tight and benzene-resistant, as well as electrically insulated. The insulating effect of the cover layer is not reduced due to the use of the seal arrangement.

Advantageous modifications of and improvements to the measuring element of the invention are possible with the measures outlined in the dependent claims. A particularly gas-tight and benzene-resistant mounting is achieved with a metallic sleeve which is connected to the solid electrolyte body to form a structural unit, with the metallic sleeve being welded to the metallic housing. The additional use of a pressure-distributing sealing ring reduces pressure peaks onto the seal arrangement. Moreover, resistance to heat corrosion is improved with the additional sealing ring. To avoid cracks in the ceramic sealing ring and/or in the glass sealing, it is also useful for the thermal expansion coefficient of the connected materials to be as close to each other as possible. It could be ascertained, however, that a slightly higher thermal expansion coefficient of the metallic sleeve is not harmful, because the resulting compressive strains can be compensated by the ceramic sealing ring.

BRIEF DESCRIPTION OF THE DRAWING

An embodiment of the invention is illustrated in the drawing and described in detail below.

DESCRIPTION OF THE PREFERRED EMBODIMENTS

Figure 1:
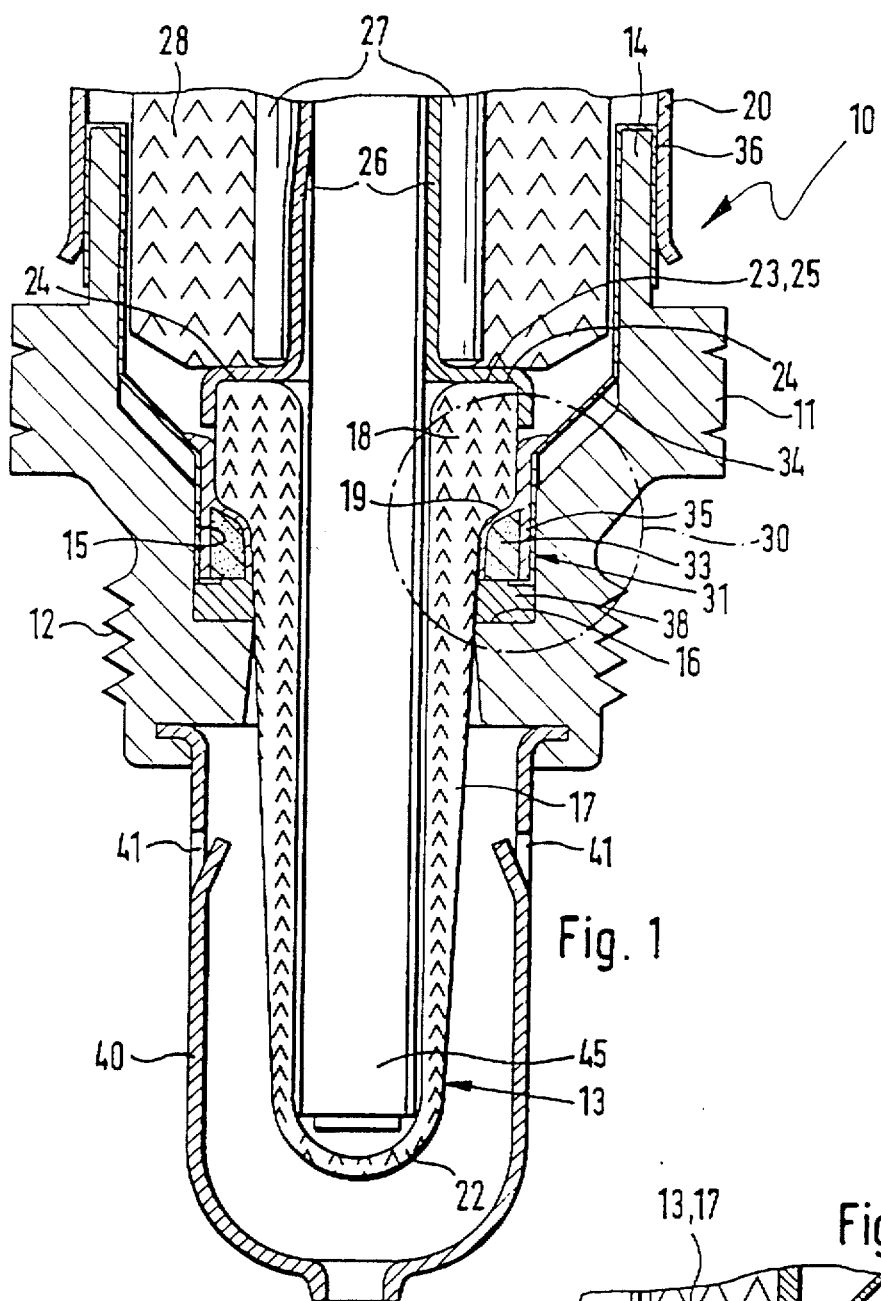
FIG. 1 shows a cross section through a part of a measuring element of the invention, the part being located on the side of the exhaust gas.
Figure 2:
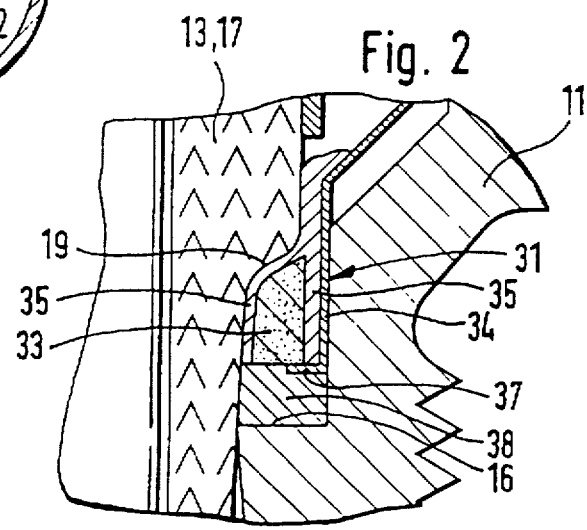
FIG. 2 shows an enlarged cutout of a seal zone in FIG. 1.

The electrochemical measuring element 10 according to FIG. 1, shown in cutout, has a metallic housing 11 having a thread 12 as securing mean for mounting in an exhaust gas pipe, not shown, and a sensor element 13. The housing 11 has a longitudinal bore 15 having a seal seat 16 on the side of the housing. A seal zone 30 shown on an enlarged scale in FIG. 2 forms at the seal seat 16 on the side of the housing, between the sensor element 13 and the housing 11. The sensor element 13 is in sealed connection with the housing 11 by means of a seal arrangement 31. The connection-side end of the housing 11 is surrounded by a cladding 20, in which the connection-side components are disposed.

The sensor element 13 is a tubular solid electrolyte body 17 whose end segment 22 on the side of the measured gas is closed. A bead-shaped head 18 having an annular end face 25 is formed onto the connection-side end segment 23. A shoulder-shaped seal seat 19, with which the sensor element 13 rests against the seal arrangement 31, is configured at the bead-shaped head 18. On the outside, which is exposed to the measured gas, a measuring electrode, not shown in detail, is disposed at the solid electrolyte body 17, and a reference electrode, likewise not shown in detail and exposed to the reference gas, for example air, is disposed on the side facing the interior. The measuring electrode and the reference electrode are respectively guided, with conductor paths which are also not shown in detail, to electrode contacts 24 disposed on the end face 25.

Contact elements 26, which are respectively contacted with a connecting cable 27, lie on the electrode contacts 24. The connecting cables 27 are guided out of the cladding 20, which is remote from the measured gas, by a sealing part, not shown, and connected to a measuring or control device. An insulating sleeve 28, preferably comprising a ceramic material, is further disposed in the longitudinal bore 15 of the housing 11. With the aid of mechanical means, not shown, the insulating sleeve 28 is pressed against the contact elements 26, producing an electrical connection to the electrode contacts 24.

The sensor element 13 protruding from the longitudinal bore 15 on the side of the measured gas is surrounded, with spacing, by a protective tube 40 that possesses openings 41 for the entrance and exit, respectively, of the measured gas, and is held at the end of the housing 11 on the side of the measured gas. The interior of the sensor element 13 is filled by, for example, a rod-shaped heating element 45 which is provided with line terminals, not shown.

The seal arrangement 31 includes a ceramic sealing ring 33, a metallic sleeve 34 and a glass sealing 35. The shape of the metallic sleeve 34 extensively simulates the contour of the longitudinal bore 15. At the connection-side end, the sleeve 34 is flanged to form an annular collar 36. The collar 36 extends around an edge 14 formed onto the housing 11. At the end on the side of the measured gas, the metallic sleeve 34 is configured to have an annular support layer 37.

Forsterite is an example of a material suitable for the ceramic sealing ring 33. Ferritic or martensitic steels are preferably used for the metallic sleeve 34. A pressed ring of steatite powder can be used as the pressure-distributing sealing ring 38. Steatite has a good resistance to heat corrosion, which protects the metallic sleeve 34 against corrosion on the side of the measured gas.

As a first step, the completely-sintered sensor element 13 is connected to the ceramic sealing ring 33, the metallic sleeve 34 and the glass sealing 35 to form a structural unit. This process involves the insertion of the ceramic sealing ring 33 into the metallic sleeve 34, with the sealing ring 33 resting on the support layer 37. The sensor element 13 is inserted into the ceramic sealing ring 33, and comes to rest, with the seal seat 19, on the sealing ring 33. Now a glass powder, for example barium silicate glass powder, is inserted into the gaps between the sensor element 13 and the sealing ring 33, and between the sealing ring 33 and the metallic sleeve 34. This arrangement is subjected to a thermal treatment, the temperature of the thermal treatment being higher than the melting temperature of the barium silicate glass. Consequently, the gas-tight glass sealing 35 forms between the sensor element 13 and the sealing ring 33, as well as between the sealing ring 33 and the metallic sleeve 34. The sensor element 13, ceramic sealing ring 33, metallic sleeve 34 and glass sealing 35 subsequently constitute a structural unit.

To produce the seal, first a pressure-distributing sealing ring 38 is positioned on the seal seat 16. Now the structural unit comprising the sensor element 13 and the seal arrangement 31 is placed onto the sealing ring 38. The collar 36 of the metallic sleeve 34 is then placed on the edge 14 of the housing 11. The cladding 20 is then pushed over the collar, and the insulating sleeve 28 additionally presses on the sensor element 13 and thus the structural unit. Consequently, pressure is exerted on the pressure-distributing sealing ring 38. In this position, in which a pressure acts on the structural unit comprising the sensor element 13, ceramic sealing ring 33, metallic sleeve 34 and glass sealing 35, the cladding 20, together with the collar 36, is welded to the housing 11 to be gas-tight, for example with laser welding.

In a further embodiment of the seal arrangement 31, the ceramic sealing ring 33 is provided on at least its inner and outer casing surface with a glass layer. Due to a thermal treatment, the glass layer changes over to a fusible phase which forms the glass sealing 35 between the sensor element 13 and the metallic sleeve 34.

What is claimed is:

1. An electrochemical measuring element for determining oxygen content in exhaust cases of internal combustion engines, comprising:

a metallic housing;

a sensor element which is a tube that is closed at one end, which is inserted into the metallic housing, and which forms a structural unit with the metallic housing;

a seal comprised of a glass sealing and a metallic sleeve, the glass sealing connecting the sensor element and the metallic sleeve in a gas-tight manner; and a ceramic sealing ring which is disposed between the sensor element and the metallic sleeve.

wherein the glass sealing is inserted between the sensor element and the ceramic sealing ring, as well as between the ceramic sealing ring and the metallic sleeve, wherein the sensor element and the seal form a preassembled structural unit which can be inserted into the metallic housing, and wherein the metallic sleeve is welded to the metallic housing in a gas-tight manner.

2. The measuring element according to claim 1, wherein the housing has an edge formed thereon, wherein the metallic sleeve has an annular collar which extends around the edge formed on the metallic housing, and wherein the metallic sleeve via the collar is welded to the metallic housing in a gas-tight manner.

3. The measuring element according to claim 2, further comprising a connection-side cladding which is positioned over the annular collar, wherein the cladding, together with the metallic sleeve, is welded to the metallic housing.

4. The measuring element according to claim 1, wherein the ceramic sealing ring is comprised of forsterite.

5. The measuring element according to claim 1, wherein the glass sealing is produced by insertion of glass powder into the gaps between the sensor element and the ceramic sealing ring and between the ceramic sealing ring and the metallic sleeve, and wherein the glass powder is brought into the fusible phase by a thermal treatment.

6. The measuring element according to claim 1, wherein the ceramic sealing ring has inside and outside casing surfaces.

wherein the ceramic sealing ring is provided on at least the inside and outside casing surfaces thereof with a glass layer, and wherein the glass layer is connected to the sensor element, on the one hand, and to the metallic sleeve, on the other hand, while molten due to thermal treatment.

7. The measuring element according to claim 1, wherein the metallic housing has a seal seat on which a pressure-distributing sealing ring is positioned, on which pressure-distributing sealing ring the ceramic sealing ring is seated.

8. The measuring element according to claim 7, wherein the pressure-distributing sealing ring is a pressed ring comprised of steatite powder.

9. The measuring element according to claim 1, wherein the glass sealing is a barium silicate glass.

* * * * *